United States Patent
Bathe et al.

(10) Patent No.: US 7,306,932 B2
(45) Date of Patent: Dec. 11, 2007

(54) CORYNEFORM BACTERIA WITH ALTERED GLUCOKINASE ACTIVITY IN THE PRODUCTION OF L-LYSINE

(75) Inventors: Brigitte Bathe, Salzkotten (DE); Stephan Hans, Osnabrück (DE); Caroline Reynen, Steinhagen (DE)

(73) Assignee: Degussa AG, Düsseldorf (DE)

( * ) Notice: Subject to any disclaimer, the term of this patent is extended or adjusted under 35 U.S.C. 154(b) by 353 days.

(21) Appl. No.: 10/498,889

(22) PCT Filed: Nov. 7, 2002

(86) PCT No.: PCT/EP02/12419

§ 371 (c)(1), (2), (4) Date: Jun. 16, 2004

(87) PCT Pub. No.: WO03/054198

PCT Pub. Date: Jul. 3, 2003

(65) Prior Publication Data

US 2005/0112732 A1    May 26, 2005

(30) Foreign Application Priority Data

Dec. 20, 2001 (DE) ................. 101 62 730

(51) Int. Cl.
- *C07H 21/02* (2006.01)
- *C12P 23/00* (2006.01)
- *C12N 15/00* (2006.01)
- *C12N 1/12* (2006.01)

(52) U.S. Cl. ................ 435/115; 435/320.1; 435/252.3; 435/254.11; 435/254.2; 435/257.1; 536/23.1

(58) Field of Classification Search .............. None
See application file for complete search history.

(56) References Cited

U.S. PATENT DOCUMENTS 6,913,910 B2    7/2005    Möckel et al.

2002/0040129 A1    4/2002    Möckel et al.
2003/0022320 A1    1/2003    Möckel et al.

FOREIGN PATENT DOCUMENTS

EP    1 106 694 A1    6/2001
EP    1 108 790 A2    6/2001

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Bischoff, J., Domrachev, M., Federhen, S., Hotton, C., Leipe, D., Soussov, V., Sternberg, R., and Turner, S., NCBI Taxonomy Browser[online]: Retrieved from the internet using "Coryneform bacteria" at <URL: http://www.ncbi.nlm.nih.gov/Taxonomy/Browser/xxxtax.cgi>.*
Pompejus et al.; "*Corynebacterium glutamicum* SMP Protein Sequence SEQ ID No: 24" DATABASE GSP 'online! EBI, Hinxton, Camdridgeshire, UK; Apr. 30, 2001.
Nakagawa et al.: "*C glutamicum* Protein Fragment SEQ ID No: 6984." DATABASE GSP 'online! EBI, Hinxton, Cambridgeshire, UK; Sep. 26, 2001.
Lee J.K. et al.: "Characterization of GLK, A Gene Coding for Glucose Kinase of *Corynebacterium glutamicium*"; Abstracts of the General Meeting of the American Society for Microbiology, American Society for Microbiology, Washington, D.C.; vol. 99, Jun. 3, 1999; p. 369.
Park Sun-Yang et al.; "Characterization of glk, a gene coding for Glucose Kinase of *Corynebacterium glutamicum*"; FEMS Microbiology Letters, Amsterdam, NL,; vol. 188, No. 2, Jul. 15, 2000.

* cited by examiner

*Primary Examiner*—Richard Hutson
*Assistant Examiner*—Jae Wan Lee
(74) *Attorney, Agent, or Firm*—Michael A. Sanzo; Law Office of Michael A. Sanzo, LLC

(57) ABSTRACT

The invention relates to alleles of the glk gene from coryneform bacteria coding for glucokinases, and to processes for the production of L-lysine by fermentation using bacteria containing such alleles.

15 Claims, 1 Drawing Sheet

Figure 1: Plasmid pK18mobsacB_glk_A213V
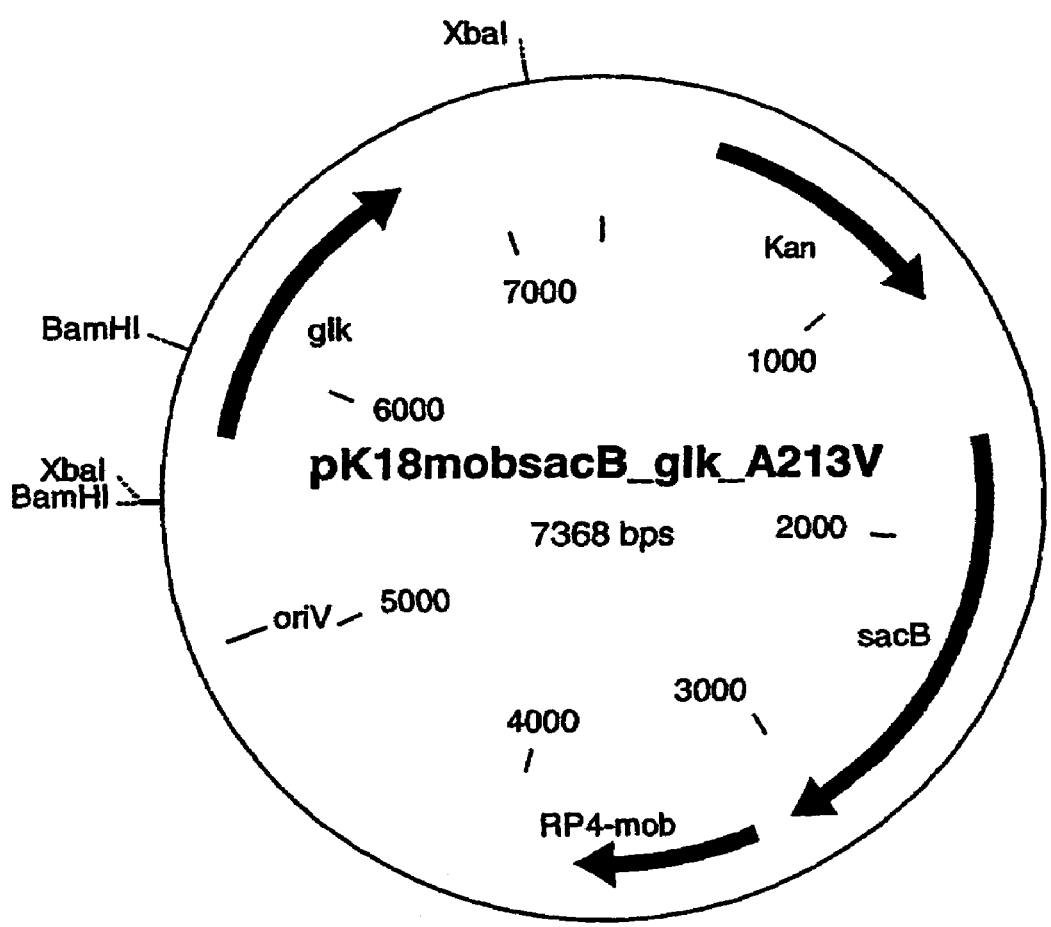

SEQUENCE LISTING

```
<160> NUMBER OF SEQ ID NOS: 8

<210> SEQ ID NO 1
<211> LENGTH: 969
<212> TYPE: DNA
<213> ORGANISM: Corynebacterium glutamicum
<220> FEATURE:
<221> NAME/KEY: CDS
<222> LOCATION: (1)..(969)
<223> OTHER INFORMATION: glk wild-type gene

<400> SEQUENCE: 1 atg cca caa aaa ccg gcc agt ttc gcg gtg ggc ttt gac atc ggc ggc      48
Met Pro Gln Lys Pro Ala Ser Phe Ala Val Gly Phe Asp Ile Gly Gly
1               5                   10                  15 acc aac atg cga gcc ggg ctt gtc gac gaa tcc ggg cgc atc gtg acc      96
Thr Asn Met Arg Ala Gly Leu Val Asp Glu Ser Gly Arg Ile Val Thr
            20                  25                  30 agt ttg tcg gcg ccg tcg ccg cgc acg acg cag gca atg gaa cag ggg     144
Ser Leu Ser Ala Pro Ser Pro Arg Thr Thr Gln Ala Met Glu Gln Gly
        35                  40                  45 att ttt gat cta gtc gaa cag ctc aag gcc gaa tac ccg gtt ggt gct     192
```

```
Ile Phe Asp Leu Val Glu Gln Leu Lys Ala Glu Tyr Pro Val Gly Ala
 50                  55                  60 gtg gga ctt gcc gtc gcg gga ttt ttg gat cct gag tgc gag gtt gtt    240
Val Gly Leu Ala Val Ala Gly Phe Leu Asp Pro Glu Cys Glu Val Val
 65                  70                  75                  80 cga ttt gcc ccg cac ctt cct tgg cgc gat gag cca gtg cgt gaa aag    288
Arg Phe Ala Pro His Leu Pro Trp Arg Asp Glu Pro Val Arg Glu Lys
                 85                  90                  95 ttg gaa aac ctt ttg ggc ctg cct gtt cgt ttg gaa cat gat gcc aac    336
Leu Glu Asn Leu Leu Gly Leu Pro Val Arg Leu Glu His Asp Ala Asn
            100                 105                 110 tca gca gcg tgg ggt gag cat cgt ttt ggt gca gct caa ggc gct gac    384
Ser Ala Ala Trp Gly Glu His Arg Phe Gly Ala Ala Gln Gly Ala Asp
            115                 120                 125 aac tgg gtt ttg ttg gca ctc ggc act gga att ggt gca gcg ctg att    432
Asn Trp Val Leu Leu Ala Leu Gly Thr Gly Ile Gly Ala Ala Leu Ile
        130                 135                 140 gaa aaa ggc gaa att tac cgt ggt gca tat ggc acg gca cca gaa ttt    480
Glu Lys Gly Glu Ile Tyr Arg Gly Ala Tyr Gly Thr Ala Pro Glu Phe
145                 150                 155                 160 ggt cat ttg cgt gtt gtt cgt ggc gga cgc gca tgt gcg tgt ggc aaa    528
Gly His Leu Arg Val Val Arg Gly Gly Arg Ala Cys Ala Cys Gly Lys
                165                 170                 175 gaa ggc tgc ctg gag cgt tac tgt tcc ggt act gcc ttg gtt tac act    576
Glu Gly Cys Leu Glu Arg Tyr Cys Ser Gly Thr Ala Leu Val Tyr Thr
            180                 185                 190 gcg cgt gaa ttg gct tcg cat ggc tca ttc cgc aac agc ggg ctg ttt    624
Ala Arg Glu Leu Ala Ser His Gly Ser Phe Arg Asn Ser Gly Leu Phe
            195                 200                 205 gac aag atc aaa gcc gat ccg aat tcc atc aat gga aaa acg atc act    672
Asp Lys Ile Lys Ala Asp Pro Asn Ser Ile Asn Gly Lys Thr Ile Thr
        210                 215                 220 gcg gca gcg cgc caa gaa gac cca ctt gct ctc gcc gtt ctg gaa gat    720
Ala Ala Ala Arg Gln Glu Asp Pro Leu Ala Leu Ala Val Leu Glu Asp
225                 230                 235                 240 ttc agc gag tgg ctg ggc gaa act ttg gcg atc att gct gat gtc ctt    768
Phe Ser Glu Trp Leu Gly Glu Thr Leu Ala Ile Ile Ala Asp Val Leu
                245                 250                 255 gac cca ggc atg atc atc att ggt ggc gga ctg tcc aat gct gcc gac    816
Asp Pro Gly Met Ile Ile Ile Gly Gly Gly Leu Ser Asn Ala Ala Asp
            260                 265                 270 ctt tat ttg gat cgc tcg gtc aac cac tat tcc acc cgc atc gtc ggc    864
Leu Tyr Leu Asp Arg Ser Val Asn His Tyr Ser Thr Arg Ile Val Gly
            275                 280                 285 gca gga tat cgc cct ttg gca cgc gtt gcc aca gct cag ttg ggt gcg    912
Ala Gly Tyr Arg Pro Leu Ala Arg Val Ala Thr Ala Gln Leu Gly Ala
        290                 295                 300 gat gct ggc atg atc ggt gtc gct gat cta gct cga cgc tct gta gtg    960
Asp Ala Gly Met Ile Gly Val Ala Asp Leu Ala Arg Arg Ser Val Val
305                 310                 315                 320 gaa gcc aac                                                        969
Glu Ala Asn <210> SEQ ID NO 2
<211> LENGTH: 323
<212> TYPE: PRT
<213> ORGANISM: Corynebacterium glutamicum

<400> SEQUENCE: 2

Met Pro Gln Lys Pro Ala Ser Phe Ala Val Gly Phe Asp Ile Gly Gly
```

```
                1               5                       10                      15
        Thr Asn Met Arg Ala Gly Leu Val Asp Glu Ser Gly Arg Ile Val Thr
                        20                      25                      30

Ser Leu Ser Ala Pro Ser Pro Arg Thr Thr Gln Ala Met Glu Gln Gly
                        35                      40                      45

Ile Phe Asp Leu Val Glu Gln Leu Lys Ala Glu Tyr Pro Val Gly Ala
                        50                      55                      60

Val Gly Leu Ala Val Ala Gly Phe Leu Asp Pro Glu Cys Glu Val Val
        65                      70                      75                      80

Arg Phe Ala Pro His Leu Pro Trp Arg Asp Glu Pro Val Arg Glu Lys
                        85                      90                      95

Leu Glu Asn Leu Leu Gly Leu Pro Val Arg Leu Glu His Asp Ala Asn
                        100                     105                     110

Ser Ala Ala Trp Gly Glu His Arg Phe Gly Ala Ala Gln Gly Ala Asp
                        115                     120                     125

Asn Trp Val Leu Leu Ala Leu Gly Thr Gly Ile Gly Ala Ala Leu Ile
                        130                     135                     140

Glu Lys Gly Glu Ile Tyr Arg Gly Ala Tyr Gly Thr Ala Pro Glu Phe
        145                     150                     155                     160

Gly His Leu Arg Val Val Arg Gly Gly Arg Ala Cys Ala Cys Gly Lys
                        165                     170                     175

Glu Gly Cys Leu Glu Arg Tyr Cys Ser Gly Thr Ala Leu Val Tyr Thr
                        180                     185                     190

Ala Arg Glu Leu Ala Ser His Gly Ser Phe Arg Asn Ser Gly Leu Phe
                        195                     200                     205

Asp Lys Ile Lys Ala Asp Pro Asn Ser Ile Asn Gly Lys Thr Ile Thr
                        210                     215                     220

Ala Ala Ala Arg Gln Glu Asp Pro Leu Ala Leu Ala Val Leu Glu Asp
        225                     230                     235                     240

Phe Ser Glu Trp Leu Gly Glu Thr Leu Ala Ile Ile Ala Asp Val Leu
                        245                     250                     255

Asp Pro Gly Met Ile Ile Ile Gly Gly Gly Leu Ser Asn Ala Ala Asp
                        260                     265                     270

Leu Tyr Leu Asp Arg Ser Val Asn His Tyr Ser Thr Arg Ile Val Gly
                        275                     280                     285

Ala Gly Tyr Arg Pro Leu Ala Arg Val Ala Thr Ala Gln Leu Gly Ala
                        290                     295                     300

Asp Ala Gly Met Ile Gly Val Ala Asp Leu Ala Arg Arg Ser Val Val
        305                     310                     315                     320

Glu Ala Asn
```

<210> SEQ ID NO 3
<211> LENGTH: 969
<212> TYPE: DNA
<213> ORGANISM: Corynebacterium glutamicum
<220> FEATURE:
<221> NAME/KEY: CDS
<222> LOCATION: (1)..(969)
<223> OTHER INFORMATION: glk allele
<220> FEATURE:
<221> NAME/KEY: mutation
<222> LOCATION: (638)..(638)
<223> OTHER INFORMATION: Replacement of cytosine by thymine

<400> SEQUENCE: 3

```
atg cca caa aaa ccg gcc agt ttc gcg gtg ggc ttt gac atc ggc ggc      48
Met Pro Gln Lys Pro Ala Ser Phe Ala Val Gly Phe Asp Ile Gly Gly
```

-continued

```
1               5                   10                  15 acc aac atg cga gcc ggg ctt gtc gac gaa tcc ggg cgc atc gtg acc    96
Thr Asn Met Arg Ala Gly Leu Val Asp Glu Ser Gly Arg Ile Val Thr
             20                  25                  30 agt ttg tcg gcg ccg tcg ccg cgc acg acg cag gca atg gaa cag ggg   144
Ser Leu Ser Ala Pro Ser Pro Arg Thr Thr Gln Ala Met Glu Gln Gly
         35                  40                  45 att ttt gat cta gtc gaa cag ctc aag gcc gaa tac ccg gtt ggt gct   192
Ile Phe Asp Leu Val Glu Gln Leu Lys Ala Glu Tyr Pro Val Gly Ala
 50                  55                  60 gtg gga ctt gcc gtc gcg gga ttt ttg gat cct gag tgc gag gtt gtt   240
Val Gly Leu Ala Val Ala Gly Phe Leu Asp Pro Glu Cys Glu Val Val
 65                  70                  75                  80 cga ttt gcc ccg cac ctt cct tgg cgc gat gag cca gtg cgt gaa aag   288
Arg Phe Ala Pro His Leu Pro Trp Arg Asp Glu Pro Val Arg Glu Lys
             85                  90                  95 ttg gaa aac ctt ttg ggc ctg cct gtt cgt ttg gaa cat gat gcc aac   336
Leu Glu Asn Leu Leu Gly Leu Pro Val Arg Leu Glu His Asp Ala Asn
         100                 105                 110 tca gca gcg tgg ggt gag cat cgt ttt ggt gca gct caa ggc gct gac   384
Ser Ala Ala Trp Gly Glu His Arg Phe Gly Ala Ala Gln Gly Ala Asp
         115                 120                 125 aac tgg gtt ttg ttg gca ctc ggc act gga att ggt gca gcg ctg att   432
Asn Trp Val Leu Leu Ala Leu Gly Thr Gly Ile Gly Ala Ala Leu Ile
 130                 135                 140 gaa aaa ggc gaa att tac cgt ggt gca tat ggc acg gca cca gaa ttt   480
Glu Lys Gly Glu Ile Tyr Arg Gly Ala Tyr Gly Thr Ala Pro Glu Phe
145                 150                 155                 160 ggt cat ttg cgt gtt gtt cgt ggc gga cgc gca tgt gcg tgt ggc aaa   528
Gly His Leu Arg Val Val Arg Gly Gly Arg Ala Cys Ala Cys Gly Lys
             165                 170                 175 gaa ggc tgc ctg gag cgt tac tgt tcc ggt act gcc ttg gtt tac act   576
Glu Gly Cys Leu Glu Arg Tyr Cys Ser Gly Thr Ala Leu Val Tyr Thr
         180                 185                 190 gcg cgt gaa ttg gct tcg cat ggc tca ttc cgc aac agc ggg ctg ttt   624
Ala Arg Glu Leu Ala Ser His Gly Ser Phe Arg Asn Ser Gly Leu Phe
         195                 200                 205 gac aag atc aaa gtc gat ccg aat tcc atc aat gga aaa acg atc act   672
Asp Lys Ile Lys Val Asp Pro Asn Ser Ile Asn Gly Lys Thr Ile Thr
 210                 215                 220 gcg gca gcg cgc caa gaa gac cca ctt gct ctc gcc gtt ctg gaa gat   720
Ala Ala Ala Arg Gln Glu Asp Pro Leu Ala Leu Ala Val Leu Glu Asp
225                 230                 235                 240 ttc agc gag tgg ctg ggc gaa act ttg gcg atc att gct gat gtc ctt   768
Phe Ser Glu Trp Leu Gly Glu Thr Leu Ala Ile Ile Ala Asp Val Leu
             245                 250                 255 gac cca ggc atg atc atc att ggt ggc gga ctg tcc aat gct gcc gac   816
Asp Pro Gly Met Ile Ile Ile Gly Gly Gly Leu Ser Asn Ala Ala Asp
         260                 265                 270 ctt tat ttg gat cgc tcg gtc aac cac tat tcc acc cgc atc gtc ggc   864
Leu Tyr Leu Asp Arg Ser Val Asn His Tyr Ser Thr Arg Ile Val Gly
         275                 280                 285 gca gga tat cgc cct ttg gca cgc gtt gcc aca gct cag ttg ggt gcg   912
Ala Gly Tyr Arg Pro Leu Ala Arg Val Ala Thr Ala Gln Leu Gly Ala
 290                 295                 300 gat gct ggc atg atc ggt gtc gct gat cta gct cga cgc tct gta gtg   960
Asp Ala Gly Met Ile Gly Val Ala Asp Leu Ala Arg Arg Ser Val Val
305                 310                 315                 320 gaa gcc aac                                                        969
Glu Ala Asn
```

<210> SEQ ID NO 4
<211> LENGTH: 323
<212> TYPE: PRT
<213> ORGANISM: Corynebacterium glutamicum

<400> SEQUENCE: 4

```
Met Pro Gln Lys Pro Ala Ser Phe Ala Val Gly Phe Asp Ile Gly Gly
1               5                   10                  15

Thr Asn Met Arg Ala Gly Leu Val Asp Glu Ser Gly Arg Ile Val Thr
            20                  25                  30

Ser Leu Ser Ala Pro Ser Pro Arg Thr Thr Gln Ala Met Glu Gln Gly
        35                  40                  45

Ile Phe Asp Leu Val Glu Gln Leu Lys Ala Glu Tyr Pro Val Gly Ala
    50                  55                  60

Val Gly Leu Ala Val Ala Gly Phe Leu Asp Pro Glu Cys Glu Val Val
65                  70                  75                  80

Arg Phe Ala Pro His Leu Pro Trp Arg Asp Glu Pro Val Arg Glu Lys
                85                  90                  95

Leu Glu Asn Leu Leu Gly Leu Pro Val Arg Leu Glu His Asp Ala Asn
            100                 105                 110

Ser Ala Ala Trp Gly Glu His Arg Phe Gly Ala Ala Gln Gly Ala Asp
        115                 120                 125

Asn Trp Val Leu Leu Ala Leu Gly Thr Gly Ile Gly Ala Ala Leu Ile
130                 135                 140

Glu Lys Gly Glu Ile Tyr Arg Gly Ala Tyr Gly Thr Ala Pro Glu Phe
145                 150                 155                 160

Gly His Leu Arg Val Val Arg Gly Gly Arg Ala Cys Ala Cys Gly Lys
                165                 170                 175

Glu Gly Cys Leu Glu Arg Tyr Cys Ser Gly Thr Ala Leu Val Tyr Thr
            180                 185                 190

Ala Arg Glu Leu Ala Ser His Gly Ser Phe Arg Asn Ser Gly Leu Phe
        195                 200                 205

Asp Lys Ile Lys Val Asp Pro Asn Ser Ile Asn Gly Lys Thr Ile Thr
210                 215                 220

Ala Ala Ala Arg Gln Glu Asp Pro Leu Ala Leu Ala Val Leu Glu Asp
225                 230                 235                 240

Phe Ser Glu Trp Leu Gly Glu Thr Leu Ala Ile Ile Ala Asp Val Leu
                245                 250                 255

Asp Pro Gly Met Ile Ile Ile Gly Gly Gly Leu Ser Asn Ala Ala Asp
            260                 265                 270

Leu Tyr Leu Asp Arg Ser Val Asn His Tyr Ser Thr Arg Ile Val Gly
        275                 280                 285

Ala Gly Tyr Arg Pro Leu Ala Arg Val Ala Thr Ala Gln Leu Gly Ala
        290                 295                 300

Asp Ala Gly Met Ile Gly Val Ala Asp Leu Ala Arg Arg Ser Val Val
305                 310                 315                 320

Glu Ala Asn
```

<210> SEQ ID NO 5
<211> LENGTH: 1655
<212> TYPE: DNA
<213> ORGANISM: Artificial sequence
<220> FEATURE:
<221> NAME/KEY: misc_feature
<222> LOCATION: (1)..(1655)
<223> OTHER INFORMATION: Description of the artificial sequence: PCR
      product of the glk allele (= glk_A213V allele)
<220> FEATURE:
<221> NAME/KEY: allele
<222> LOCATION: (215)..(1183)
<223> OTHER INFORMATION: glk allele
<220> FEATURE:
<221> NAME/KEY: mutation
<222> LOCATION: (852)..(852)
<223> OTHER INFORMATION: Replacement of cytosine by thymine

<400> SEQUENCE: 5

```
gatctagagc ttctcgacga tccgatccgc cgcgccgcga tgggcgctgc aggtagggcg      60
catgtggagg ccgaatggtc gtgggaaatc atggggagc ggttgaccaa tattttgcag     120
agtgaaccac gatgatggtt ggacagctgt tgatagctat actttgaaag attaaattca    180
cctaaatcct gtgtagaacg cgaggggcac tcttatgcca caaaaccgg ccagtttcgc     240
ggtgggcttt gacatcggcg gcaccaacat gcgagccggg cttgtcgacg aatccgggcg    300
catcgtgacc agtttgtcgg cgccgtcgcc gcgcacgacg caggcaatgg aacagggat    360
ttttgatcta gtcgaacagc tcaaggccga atacccggtt ggtgctgtgg gacttgccgt    420
cgcgggattt ttggatcctg agtgcgaggt tgttcgattt gccccgcacc ttccttggcg    480
cgatgagcca gtgcgtgaaa agttggaaaa ccttttgggc ctgcctgttc gtttggaaca    540
tgatgccaac tcagcagcgt ggggtgagca tcgttttggt gcagctcaag gcgctgacaa    600
ctgggttttg ttggcactcg gcactggaat tggtgcagcg ctgattgaaa aaggcgaaat    660
ttaccgtggt gcatatggca cggcaccaga atttggtcat ttgcgtgttg ttcgtggcgg    720
acgcgcatgt gcgtgtggca agaaggctg cctggagcgt tactgttccg gtactgcctt     780
ggtttacact gcgcgtgaat tggcttcgca tggctcattc cgcaacagcg ggctgtttga    840
caagatcaaa gtcgatccga attccatcaa tggaaaaacg atcactgcgg cagcgcgcca    900
agaagaccca cttgctctcg ccgttctgga agatttcagc gagtggctgg gcgaaacttt    960
ggcgatcatt gctgatgtcc ttgacccagg catgatcatc attggtggcg gactgtccaa   1020
tgctgccgac cttttattgg atcgctcggt caaccactat tccacccgca tcgtcggcgc   1080
aggatatcgc cctttggcac gcgttgccac agctcagttg ggtgcggatg ctggcatgat   1140
cggtgtcgct gatctagctc gacgctctgt agtggaagcc aactaggtgt ttttcggtgg   1200
gctgcgatga cgcatgtcca ccaaaagagc cacccttaa agaaattaaa agtggtttt    1260
ggtagcttcg cagcaaaata cacatcgtgg gtaacgtatt cttagaagtt cctacagcag   1320
taaagcgcga agaagggta acccaaaca tcatgaaaaa caactggtat cggcttttca    1380
agtatgtgct aattggcccg tttttgcgtg tgtacaaccg cccggagatc gaaggcaaag   1440
aaaacatccc tgcagaaggt gccgcgatca tggcgtccaa ccacgaagca gtgatggatt   1500
cctttttattt tccctgctg tgcccacggc agctgacctt cccagcgaag gccgaatact   1560
tcacatcacc aggtattaaa ggcaagatgc agaagtggtt ttttacttct gtggggcaag   1620
tacccctgga ccgcaccgca gataatgtct agatc                              1655
```

<210> SEQ ID NO 6
<211> LENGTH: 28
<212> TYPE: DNA
<213> ORGANISM: Artificial sequence
<220> FEATURE:
<221> NAME/KEY: misc_feature
<222> LOCATION: (1)..(28)
<223> OTHER INFORMATION: Description of the artificial sequence: primer -continued

```
glk_XL-A1

<400> SEQUENCE: 6
gatctagagc ttctcgacga tccgatcc                                          28

<210> SEQ ID NO 7
<211> LENGTH: 28
<212> TYPE: DNA
<213> ORGANISM: Artificial sequence
<220> FEATURE:
<221> NAME/KEY: misc_feature
<222> LOCATION: (1)..(28)
<223> OTHER INFORMATION: Description of the artificial sequence: primer
      glk_XL-A2

<400> SEQUENCE: 7
gatctagaca ttatctgcgg tgcggtcc                                          28

<210> SEQ ID NO 8
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: Description of the artificial sequence: primer
      gl1

<400> SEQUENCE: 8
ggaacatgat gccaactcag                                                   20
```

US 7,306,932 B2

CORYNEFORM BACTERIA WITH ALTERED GLUCOKINASE ACTIVITY IN THE PRODUCTION OF L-LYSINE

CROSS REFERENCE TO RELATED APPLICATIONS

The present application represents U.S. national stage of international application PCT/EP02/12419, which had an international filing date of Nov. 7, 2002 and which was published in English under PCT Article 21(2) on Jul. 3, 2003. The international application claims priority to German application 101 62 730.0, filed on Dec. 20, 2001.

FIELD OF THE INVENTION

The invention provides alleles of the glk gene from coryneform bacteria coding for variants of glucokinase, and processes for the production of L-lysine by fermentation using bacteria containing such alleles.

PRIOR ART

The amino acid L-lysine is used in human medicine and in the pharmaceuticals industry, in the foodstuffs industry and, very especially, in the feeding of animals.

It is known that amino acids are produced by fermentation of strains of coryneform bacteria, especially *Corynebacterium glutamicum*. Because of their great importance, attempts are continuously being made to improve the production processes. Improvements to the processes may concern measures relating to the fermentation, such as, for example, stirring and oxygen supply, or the composition of the nutrient media, such as, for example, the sugar concentration during the fermentation, or working up to the product form by, for example, ion-exchange chromatography, or the intrinsic performance properties of the microorganism itself.

In order to improve the performance properties of such microorganisms, methods of mutagenesis, selection and mutant selection are employed. Such methods yield strains which are resistant to antimetabolites or are auxotrophic for metabolites that are important in terms of regulation, and which produce amino acids. A known antimetabolite is the lysine analogue S-(2-aminoethyl)-L-cysteine (AEC).

For a number of years, methods of recombinant DNA technology have also been used for improving the strain of L-amino acid-producing strains of *Corynebacterium*, by amplifying individual amino acid biosynthesis genes and studying the effect on amino acid production.

The nucleotide sequence of the gene coding for the glucokinase of *Corynebacterium glutamicum* can be found in patent application WO 01/00844 under the Identification Code RXA02149 as Sequence No. 23.

The nucleotide sequence of the gene coding for the glucokinase of *Corynebacterium glutamicum* can also be found in patent application EP-A-1108790 as Sequence No. 3484 and as Sequence No. 7066.

The nucleotide sequence has also been deposited in the data bank of the National Center for Biotechnology Information (NCBI) of the National Library of Medicine (Bethesda, Md., USA) under Accession Number AX064897 and under Accession Number AX123568.

The favorable action of the overexpression of the glk gene on lysine production is shown in EP-A-1106694.

OBJECT OF THE INVENTION

The inventors have set themselves the object of providing novel measures for the improved production of L-lysine by fermentation.

SUMMARY OF THE INVENTION

Where L-lysine or lysine is mentioned hereinbelow, it is to be understood as meaning not only the bases but also the salts, such as, for example, lysine monohydrochloride or lysine sulfate.

The invention provides replicable nucleotide sequences (DNA) originating from coryneform bacteria, especially *Corynebacterium glutamicum*, and coding for the enzyme glucokinase, wherein the associated amino acid sequences in SEQ ID No. 2 contain at position 213 any proteinogenic amino acid, with the exception of L-alanine.

Proteinogenic amino acids are understood as being the amino acids which occur in naturally occurring proteins, that is to say in proteins of microorganisms, plants, animals and humans. They include the amino acids L-glycine, L-alanine, L-valine, L-leucine, L-isoleucine, L-serine, L-threonine, L-cysteine, L-methionine, L-proline, L-phenylalanine, L-tyrosine, L-tryptophan, L-asparagine, L-glutamine, L-aspartic acid, L-glutamic acid, L-arginine, L-lysine, L-histidine and L-selenocysteine.

The invention also provides a replicable nucleotide sequence (DNA) originating from coryneform bacteria, especially *Corynebacterium glutamicum*, and coding for the enzyme glucokinase, wherein the associated amino acid sequence contains L-valine at position 213, shown in SEQ ID No. 4.

The invention also provides a replicable nucleotide sequence (DNA) originating from coryneform bacteria, especially *Corynebacterium glutamicum*, and coding for the enzyme glucokinase, the base sequence of which contains thymine at position 638, shown in SEQ ID No. 3.

The invention also provides plasmids (vectors) which contain the nucleotide sequences according to the invention and optionally replicate in coryneform bacteria.

The invention also provides coryneform bacteria which contain the nucleotide sequences according to the invention and in which the nucleotide sequences coding for glucokinase are optionally in overexpressed form, wherein the associated amino acid sequences contain a different proteinogenic amino acid at position 213 of SEQ ID No. 2.

Overexpression is understood as meaning an increase in the intracellular concentration or activity of the glucokinases according to the invention.

DETAILED DESCRIPTION OF THE INVENTION

By the measures of overexpression, the activity or concentration of the corresponding protein is generally increased by at least 10%, 25%, 50%, 75%, 100%, 150%, 200%, 300%, 400% or 500%, at the maximum up to 1000% or 2000%, based on the activity or concentration of the protein in the starting microorganism.

In order to achieve overexpression, the copy number of the corresponding genes can be increased, or the promoter and regulation region or the ribosome binding site, which is located upstream of the structural gene, can be mutated. Expression cassettes inserted upstream of the structural gene have the same effect. By means of inducible promoters it is additionally possible to increase the expression in the course of the production of L-lysine by fermentation. Expression is also improved by measures to prolong the life of the m-RNA. Furthermore, the enzyme activity is also enhanced by preventing degradation of the enzyme protein. The genes or gene constructs may either be present in plasmids with a different copy number or be integrated and amplified in the chromosome. Alternatively, overexpression of the genes in question may also be achieved by changing the composition of the medium and the manner in which culturing is carried out.

For increasing the copy number of the glk alleles according to the invention, plasmids which are replicated in coryneform bacteria are suitable. Many known plasmid vectors, such as, for example, pZ1 (Menkel et al., Applied and Environmental Microbiology (1989) 64: 549-554), pEKEx1 (Eikmanns et al., Gene 102:93-98 (1991)) or pHS2-1 (Sonnen et al., Gene 107:69-74 (1991)), are based on the cryptic plasmids pHM1519, pBL1 or pGA1. Other plasmid vectors, such as, for example, those which are based on pCG4 (U.S. Pat. No. 4,489,160) or pNG2 (Serwold-Davis et al., FEMS Microbiology Letters 66, 119-124 (1990)) or pAG1 (U.S. Pat. No. 5,158,891), can be used in the same manner.

For increasing the copy number it is also possible to use the method of chromosomal gene amplification, as has been described, for example, by Reinscheid et al. (Applied and Environmental Microbiology 60, 126-132 (1994)) for the duplication or amplification of the hom-thrB operon. In that method, the complete gene or allele is cloned into a plasmid vector that is able to replicate in a host (typically *E. coli*), but not in *C. glutamicum*. Suitable vectors are, for example, pSUP301 (Simon et al., Bio/Technology 1, 784-791 (1983)), pK18mob or pK19mob (Schäfer et al., Gene 145, 69-73 (1994)), PGEM-T (Promega Corporation, Madison, Wis., USA), pCR2.1-TOPO (Shuman, Journal of Biological Chemistry 269:32678-84 (1994); U.S. Pat. No. 5,487,993), pCR®Blunt (Invitrogen, Groningen, Netherlands; Bernard et al., Journal of Molecular Biology, 234: 534-541 (1993)), pEM1 (Schrumpf et al., Journal of Bacteriology 173:4510-4516 (1991)) or pBGS8 (Spratt et al., Gene 41: 337-342 (1986)). The plasmid vector containing the gene or allele to be amplified is then transferred to the desired strain of *C. glutamicum* by conjugation or transformation. The method of conjugation is described, for example, in Schafer et al. (Applied and Environmental Microbiology 60, 756-759 (1994)). Methods of transformation are described, for example, in Thierbach et al. (Applied Microbiology and Biotechnology 29, 356-362 (1988)), Dunican and Shivnan (Bio/Technology 7, 1067-1070 (1989)) and Tauch et al. (FEMS Microbiological Letters 123, 343-347 (1994)). After homologous recombination by means of a "cross-over" event, the resulting strain contains at least two copies of the gene or allele in question.

The invention provides replicable, especially endogenous, nucleotide sequences (DNA) originating from coryneform bacteria and coding for the enzyme glucokinase, wherein in the associated amino acid sequences L-alanine at position 213 of SEQ ID No. 2 is replaced by a different proteinogenic amino acid, especially L-valine, shown in SEQ ID No. 4. The invention also provides replicable, preferably endogenous, nucleotide sequences (DNA) originating from coryneform bacteria and coding for the enzyme glucokinase, the associated base sequence of which contains thymine at position 638, shown in SEQ ID No. 3.

"Endogenous genes" or "endogenous nucleotide sequences" are understood as being the genes or nucleotide sequences present in the population of a species.

The invention relates also to vectors (plasmids) which contain the mentioned nucleotide sequences and optionally replicate in coryneform bacteria.

Also claimed are coryneform bacteria in which the mentioned nucleotide sequences coding for enzyme glucokinase, are preferably in overexpressed form.

The invention provides a process for the production of L-lysine or of feed additives containing L-lysine, in which the following steps are generally carried out:

a) fermentation of coryneform bacteria containing endogenous nucleotide sequences coding for the enzyme glucokinase, wherein in the associated amino acid sequences L-alanine at position 213 has been replaced by a different proteinogenic amino acid, preferably L-valine.

The alleles of the endogenous glucokinase gene are. overexpressed under conditions suitable for the formation of the enzyme glucokinase.

b) concentration of the L-lysine in the fermentation liquor, c) isolation of the L-lysine or of the feed additive containing L-lysine from the fermentation liquor, optionally d) with constituents of the fermentation liquor and/or the biomass (>0 to 100%).

Proteinogenic amino acids are to be understood as being all amino acids that are constituents of proteins or polypeptides. They are especially: L-aspartic acid, L-asparagine, L-threonine, L-serine, L-glutamic acid, L-glutamine, glycine, L-alanine, L-cysteine, L-valine, L-methionine, L-isoleucine, L-leucine, L-tyrosine, L-phenylalanine, L-histidine, L-lysine, L-tryptophan, L-proline and L-arginine.

The wild form of the glk gene is contained in wild-type strains of coryneform bacteria, especially of the genus *Corynebacterium*. It is shown in SEQ ID No. 1. The wild-type protein is shown in SEQ ID No. 2.

Of the genus *Corynebacterium*, special mention is to be made of the species *Corynebacterium glutamicum*, which is known in the specialist field. Known wild-type strains of the species *Corynebacterium glutamicum* are, for example,

*Corynebacterium glutamicum* ATCC13032
*Corynebacterium acetoglutamicum* ATCC15806
*Corynebacterium acetoacidophilum* ATCC13870
*Corynebacterium melassecola* ATCC17965
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020.

Strains having the designation "ATCC" can be obtained from the American Type Culture Collection (Manassas, Va., USA). Strains having the designation "FERM" can be obtained from the National Institute of Advanced Industrial Science and Technology (AIST Tsukuba Central 6, 1-1-1 Higashi, Tsukuba Ibaraki, Japan). The mentioned strain of *Corynebacterium thermoaminogenes* (FERM BP-153.9) is described in U.S. Pat. No. 5,250,434.

For the production of the glk alleles according to the invention which code for variants of glucokinase, characterized by an amino acid replacement at position 213 of SEQ ID No. 2, methods of mutagenesis described in the prior art are used.

It is possible to use for the mutagenesis conventional in vivo processes of mutagenesis using mutagenic substances such as, for example, N-methyl-N'-nitro-N-nitrosoguanidine or ultraviolet light.

It is also possible to use for the mutagenesis in vitro methods, such as, for example, treatment with hydroxylamine (Miller, J. H.: A Short Course in Bacterial Genetics.

A Laboratory Manual and Handbook for *Escherichia coli* and Related Bacteria, Cold Spring Harbor Laboratory Press, Cold Spring Harbor, 1992) or mutagenic oligonucleotides (T. A. Brown: Gentechnologie für Einsteiger, Spektrum Akademischer Verlag, Heidelberg, 1993) or the polymerase chain reaction (PCR), as is described in the handbook of Newton and Graham (PCR, Spektrum Akademischer Verlag, Heidelberg, 1994). Further instructions for the production of mutations can be found in the prior art and in known textbooks of genetics and molecular biology, such as, for example, the textbook of Knippers ("Molekulare Genetik", 6th edition, Georg Thieme Verlag, Stuttgart, Germany, 1995), that of Winnacker ("Gene und Klone", VCH Verlagsgesellschaft, Weinheim, Germany, 1990) or that of Hagemann ("Allgemeine Genetik", Gustav Fischer Verlag, Stuttgart, 1986). When in vitro methods are used, the glk gene described in the prior art is amplified by means of the polymerase chain reaction starting from isolated total DNA of a wild-type strain and is optionally cloned into suitable plasmid vectors, and the DNA is subsequently subjected to the mutagenesis process. The person skilled in the art will find instructions for the amplification of DNA sequences by means of the polymerase chain reaction (PCR) inter alia in the handbook of Gait: Oligonucleotide Synthesis: A Practical Approach (IRL Press, Oxford, UK, 1984) and in Newton and Graham: PCR (Spektrum Akademischer Verlag, Heidelberg, Germany, 1994). Suitable glk alleles are subsequently selected and studied using the above-described processes. The invention provides a novel glk allele coding for a variant of glucokinase, which allele is shown in SEQ ID No. 3. The glk alleles according to the invention can be transferred into suitable strains by the method of gene replacement, as is described in Schwarzer and Pühler (Bio/Technology 9, 84-87 (1991)) or Peters-Wendisch et al. (Microbiology 144, 915-927 (1998)). In that method, the appropriate glk allele is cloned into a vector that is not replicative for *C. glutamicum*, such as, for example, pK18mobsacB or pK19mobsacB (Jäger et al., Journal of Bacteriology 174: 5462-65 (1992)) or pCR®Blunt (Invitrogen, Groningen, Netherlands; Bernard et al., Journal of Molecular Biology, 234: 534-541 (1993)) and the vector is then transferred into the desired host of *C. glutamicum* by transformation or conjugation. After homologous recombination by means of a first "cross-over" event effecting integration and a suitable second "cross-over" event effecting an excision in the target gene or in the target sequence, incorporation of the mutation is achieved. It may additionally be advantageous for the production of L-amino acids, in addition to using the glk alleles according to the invention, at the same time to enhance, especially overexpress, one or more enzymes of the biosynthesis pathway in question, of glycolysis, of the anaplerotic pathway, of the citric acid cycle, of the pentose phosphate cycle, of amino acid export and, optionally, regulatory proteins. The use of endogenous genes is generally preferred. "Endogenous genes" or "endogenous nucleotide sequences" are understood as being the genes or nucleotide sequences and alleles present in the population of a species. The term "enhancement" in this context describes the increase of the intracellular activity of one or more enzymes (proteins) in a microorganism that are coded for by the corresponding DNA, by, for example, increasing the copy number of the gene or genes, using a strong promoter or using a gene or allele that codes for a corresponding enzyme (protein) having a high level of activity, and optionally by combining those measures. By the measures of enhancement, especially overexpression, the activity or concentration of the corresponding protein is generally increased by at least 10%, 25%, 50%, 75%, 100%, 150%, 200%, 300%, 400% or 500%, at the maximum up to 1000% or 2000%, based on that of the wild-type protein or on the activity or concentration of the protein in the starting microorganism. Accordingly, for the production of L-lysine, in addition to using the variant of the glk gene, it is also possible at the same time to enhance, especially overexpress, one or more genes selected from the group.

the gene dapA coding for dihydrodipicolinate synthase (EP-B 0 197 335), the gene gap coding for glyceraldehyde-3-phosphate dehydrogenase (Eikmanns (1992), Journal of Bacteriology 174:6076-6086), the gene eno coding for enolase (EP-A-1090998), the gene tpi coding for triose phosphate isomerase (Eikmanns (1992), Journal of Bacteriology 174:6076-6086), the gene pgk coding for 3-phosphoglycerate kinase (Eikmanns (1992), Journal of Bacteriology 174:6076-6086), the gene zwf coding for glucose-6-phosphate dehydrogenase (JP-A-09224661, EP-A-1108790, WO 01/70995, WO 01/98472, WO 01/04322), the gene pyc coding for pyruvate carboxylase (DE-A-198 31 609, EP-A-1108790), the gene mqo coding for malate quinone oxidoreductase (Molenaar et al., European Journal of Biochemistry 254, 395-403 (1998), EP-A-1038969), the gene lysC coding for a feed-back resistant aspartate kinase (Accession No. P26512; EP-B-0387527; EP-A-0699759; WO 00/63388), the gene lysE coding for the lysine export protein (DE-A-195 48 222, Vrljic et al., Molecular Microbiology 22(5), 815-826 (1996)), the gene zwa1 coding for the Zwa1 protein (EP-A-1111062), the gene gnd coding for 6-phosphogluconate dehydrogenase (WO 01/71012), the gene opcA coding for a sub-unit of glucose-6-phosphate dehydrogenase (Sequence No. 79 from WO 01/00844; WO 01/04322) The enhancement of 6-phosphogluconate dehydrogenase can also be achieved, inter alia, by amino acid replacements, such as, for example, by the replacement of L-proline by L-serine, L-leucine, L-isoleucine or L-threonine at position 158 of the enzyme protein, and/or by the replacement of L-serine by L-phenylalanine or L-tyrosine at position 361 of the enzyme protein. The enhancement of the sub-unit of glucose-6-phosphate dehydrogenase, for which the gene opcA codes, can also be achieved, inter alia, by amino acid replacements, such as, for example, by the replacement of L-serine by L-phenylalanine or L-tyrosine at position 312 of the enzyme protein.

It may also be advantageous for the production of L-lysine, in addition to using the alleles of the glk gene according to the invention, at the same time to attenuate, especially diminish the expression of, one or more endogenous genes selected from the group the gene pck coding for phosphoenol pyruvate carboxykinase (EP-A-1094111), the gene pgi coding for glucose-6-phosphate isomerase (EP-A-1087015, WO 01/07626, EP-A-1108790), the gene poxB coding for pyruvate oxidase (EP-A-1096013), the gene zwa2 coding for the Zwa2 protein (EP-A-1106693), the gene fda coding for fructose-1,6-bisphosphate aldolase (Accession No. X17313; von der Osten et al., Molecular Microbiology 3 (11), 1625-1637 (1989)), the gene hom coding for homoserine dehydrogenase (EP-A-0131171), the gene thrB coding for homoserine kinase (Peoples, O. W., et al., Molecular Microbiology 2 (1988): 63-72) and the gene pfkb coding for phosphofructokinase (Sequence No. 57 from WO 01/00844). PARA0The term "attenuation" in this context describes the diminution or exclusion of the intracellular activity of one or more enzymes (proteins) in a microorganism that are coded for by the corresponding DNA, by, for example, using a weak promoter or using a gene or allele that codes for a corresponding enzyme having a low level of activity, or by inactivating the corresponding gene or enzyme (protein), and optionally by combining those measures. PARA0By the measures of attenuation, the activity or concentration of the corresponding protein is generally lowered to 0 to 75%, 0 to 50%, 0 to 25%, 0 to 10% or 0 to 5% of the activity or concentration of the wild-type protein, or of the activity or concentration of the protein in the starting microorganism. PARA0The attenuation of phosphofructokinase can also be achieved, inter alia, by amino acid replacements, such as, for example, by the replacement of L-leucine by L-alanine, L-glycine or L-proline at position 109 of the enzyme protein. PARA0The microorganisms produced according to the invention also form part of the invention and can be cultivated continuously or discontinuously by the batch process or by the fed batch or repeated fed batch process for the purposes of the production of L-amino acids. A summary of known cultivation methods is described in the textbook of Chmiel (Bioprozesstechnik 1. Einführung in die Bioverfahrenstechnik (Gustav Fischer Verlag, Stuttgart, 1991)) or in the textbook of Storhas (Bioreaktoren und periphere Einrichtungen (Vieweg Verlag, Braunschweig/Wiesbaden, 1994)). PARA0The culture medium to be used must meet the requirements of the strains in question in a suitable manner. Descriptions of culture media for various microorganisms are to be found in the handbook "Manual of Methods for General Bacteriology" of the American Society for Bacteriology (Washington D.C., USA, 1981). PARA0There may be used as the carbon source sugars and carbohydrates, such as, for example, glucose, saccharose, lactose, fructose, maltose, molasses, starch and cellulose, oils and fats, such as, for example, soybean oil, sunflower oil, groundnut oil and coconut oil, fatty acids, such as, for example, palmitic acid, stearic acid and linoleic acid, alcohols, such as, for example, glycerol and ethanol, and organic acids, such as, for example, acetic acid. Those substances may be used individually or in the form of a mixture. PARA0There may be used as the nitrogen source organic nitrogen-containing compounds, such as peptones, yeast extract, meat extract, malt extract, corn steep liquor, soybean flour and urea, or inorganic compounds, such as ammonium sulfate, ammonium chloride, ammonium phosphate, ammonium carbonate and ammonium nitrate. The nitrogen sources may be used individually or in the form of a mixture. PARA0There may be used as the phosphorus source phosphoric acid, potassium dihydrogen phosphate or dipotassium hydrogen phosphate or the corresponding sodium-containing salts. The culture medium must also contain salts of metals, such as, for example, magnesium sulfate or iron sulfate, which are necessary for growth. Finally, essential growth substances, such as amino acids and vitamins, may be used in addition to the above-mentioned substances. Suitable precursors may also be added to the culture medium. The mentioned substances may be added to the culture in the form of a single batch, or they may be suitably fed in during the cultivation. PARA0In order to control the pH of the culture, basic compounds, such as sodium hydroxide, potassium hydroxide, ammonia or ammonia water, or acid compounds, such as phosphoric acid or sulfuric acid, are expediently used. In order to control the development of foam, anti-foams, such as, for example, fatty acid polyglycol esters, may be used. In order to maintain the stability of plasmids, suitable substances having a selective action, such as, for example, antibiotics, may be added to the medium. In order to maintain aerobic conditions, oxygen or gas mixtures containing oxygen, such as, for example, air, are introduced into the culture. The temperature of the culture is normally from 20° C. to 45° C. and preferably from 25° C. to 40° C. The culture is continued until the maximum amount of the desired product has formed. That aim is normally achieved within a period of from 10 hours to 160 hours. PARA0Methods of determining L-amino acids are known from the prior art. The analysis may be carried out, for example, as described in Spackman et al. (Analytical Chemistry, 30, (1958), 1190) by anion-exchange chromatography with subsequent ninhydrin derivation, or it may be carried out by reversed phase HPLC, as described in Lindroth et al. (Analytical Chemistry (1979) 51: 1167-1174). PARA0The process according to the invention is used for the production of L-lysine by fermentation. PARA0The concentration of L-lysine can optionally be adjusted to the desired value by the addition of L-lysine. PARA0The present invention is explained in greater detail below by means of embodiment examples.

EXAMPLE 1

Amplification and sequencing of the DNA of the glk allele of strain DM1454

The *Corynebacterium glutamicum* strain DM1454 was prepared from *C. glutamicum* ATCC13032 by repeated, undirected mutagenesis, selection and mutant selection. The strain is resistant to the lysine analogue S-(2-aminoethyl)-L-cysteine.

Chromosomal DNA is isolated from strain DM1454 by the conventional methods (Eikmanns et al., Microbiology 140: 1817-1828 (1994)). By means of the polymerase chain reaction, a DNA section carrying the glk gene or allele is amplified. On the basis of the sequence of the glk gene known for *C. glutamicum* (Sequence No. 3484 and Sequence No. 7066 from EP-A-1108790), the following primer oligonucleotides are selected for the PCR:

```
                                    (SEQ ID No. 6)
glk_XL-A1:
5' ga tct aga-gct tct cga cga tcc gat cc 3'

(SEQ ID No. 7)
glk_XL-A2:
5' ga tct aga-cat tat ctg cgg tgc ggt cc 3'
```

The primers shown are synthesized by MWG Biotech (Ebersberg, Germany), and the PCR reaction is carried out according to the standard PCR method of Innis et al. (PCR protocols. A Guide to Methods and Applications, 1990, Academic Press). The primers allow the amplification of a DNA section having a length of approximately 1.65 kb and carrying the glk gene or allele. The primers additionally contain the sequence for a cleavage site of the restriction endonuclease xbaI, which is marked in the nucleotide sequence shown above by underlining.

The amplified DNA fragment having a length of approximately 1.65 kb, which carries the glk allele of strain DM1454, is identified by electrophoresis in a 0.8% agarose gel, isolated from the gel and purified by conventional methods (QIAquick Gel Extraction Kit, Qiagen, Hilden).

The nucleotide sequence of the amplified DNA fragment, or PCR product, is determined by MWG Biotech (Ebersberg, Germany) by sequencing. The sequence of the PCR product is shown in SEQ ID No. 5. The sequence of the coding region is additionally shown in SEQ ID No. 3. The amino acid sequence of the associated glucokinase protein, determined by means of the Patentin program, is shown in SEQ ID No. 4.

At position 638 of the nucleotide sequence of the coding region of the glk allele of strain DM1454 there is the base thymine (SEQ ID No. 3). At the corresponding position of the wild-type gene there is the base cytosine (SEQ ID No. 1).

At position 213 of the amino acid sequence of the glucokinase protein of strain DM1454 there is the amino acid valine (SEQ ID No. 4). At the corresponding position of the wild-type protein there is the amino acid alanine (SEQ ID No. 2).

The glk allele, which contains the base thymine at position 638 of the coding region and accordingly codes for a glucokinase protein which contains the amino acid valine at position 213 of the amino acid sequence, is referred to hereinbelow as the glk_A213V allele. In the designation "glk_A213V", A represents alanine, V represents L-valine and 213 indicates the position of the amino acid replacement (see SEQ ID No. 2 and 4).

EXAMPLE 2

Replacement of the glk wild-type gene of strain DSM5715 by the glk_A213V allele 2.1 Construction of the Replacement Vector pK18mobsacB_glk_A213V The DNA fragment approximately 1.65 kb in length which is described in Example 1 and was prepared by means of PCR and which carries the glk_A213V allele is inserted into the chromosome of C. glutamicum strain DS15715 by means of replacement mutagenesis with the aid of the sacB system described in Schafer et al. (Gene, 14, 69-73 (1994)). This system allows the preparation or selection of allele replacements which take place by homologous recombination. Strain DSM5715 is a leucine-requiring, aminoethylcysteine-resistant and L-lysine-producing mutant of Corynebacterium glutamicum ATCC13032. The strain is described in EP-A-0435 132.

To that end, the glk_A213V fragment approximately 1.65 kb in size is cleaved with restriction endonuclease XbaI, identified by electrophoresis in a 0.8% agarose gel, and then isolated from the gel and purified by conventional methods (QIAquick Gel Extraction Kit, Qiagen, Hilden).

The mobilizable cloning vector pK18mobsacB is digested with restriction enzyme XbaI and the ends are dephosphorylated with alkaline phosphatase (Alkaline Phosphatase, Boehringer Mannheim, Germany). The vector so prepared is mixed with the approximately 1.6 kb glk_A213V fragment and the batch is treated with T4-DNA ligase (Amersham-Pharmacia, Freiburg, Germany).

E. coli strain S17-1 (Simon et al., Bio/Technology 1: 784-791, 1993) is then transformed with the ligation batch (Hanahan, In. DNA cloning A practical approach. Vol.1. ILR-Press, Cold Spring Harbor, N.Y., 1989). Selection of the plasmid-carrying cells is carried out by plating out the transformation batch on LB agar (Sambrook et al., Molecular Cloning: A Laboratory Manual. $2^{nd}$ Ed. Cold Spring Harbor, N.Y., 1989) supplemented with 25 mg/l kanamycin.

Plasmid DNA is isolated from a transformant by means of the QIAprep Spin Miniprep Kit from Qiagen and is checked by restriction cleavage with the enzyme BamHI and subsequent agarose gel electrophoresis. The plasmid is named pK18mobsacB_glk_A213V and is shown in FIG. 1.

2.2 Allele Replacement

The vector pK18mobsacB_glk_A213V mentioned in Example 2.1 is transferred into C. glutamicum strain DSM5715 by conjugation according to a protocol of Schafer et al. (Journal of Microbiology 172: 1663-1666.(1990)). The vector cannot replicate independently in DSM5715 and is only retained in the cell if it has been integrated into the chromosome as the result of a recombination event. The selection of transconjugants, i.e. of clones having integrated pK18mobsacB_glk_A213V, is carried out by plating out the conjugation batch on LB agar (Sambrook et al., Molecular Cloning: A Laboratory Manual. $2^{nd}$ Ed. Cold Spring Harbor, N.Y., 1989) supplemented with 15 mg/l kanamycin and 50 mg/l nalidixic acid. Kanamycin-resistant transconjugants are spread onto LB agar plates with 25 mg/l kanamycin and incubated for 24 hours at 33° C. For the selection of mutants in which the excision of the plasmid has taken place as a result of a second recombination event, the clones are cultivated non-selectively in LB liquid medium for 30 hours, then spread onto LB agar with 10% sucrose and incubated for 16 hours.

Plasmid pK18mobsacB_glk_A213V, like the starting plasmid pK18mobsacB, contains, in addition to the kanamycin resistance gene, a copy of the sacB gene coding for levan sucrase from Bacillus subtilis. The sucrose-inducible expression leads to the formation of levan sucrase, which catalyses the synthesis of the product levan, which is toxic for C. glutamicum. Therefore, only those clones in which the integrated pK18mobsacB_glk_A213V has excised as a result of a second recombination event grow on LB agar with sucrose. In dependence on the position of the second recombination occurrence in relation to the site of mutation, the allele replacement or the incorporation of the mutation takes place at the excision, or the original copy remains in the chromosome of the host.

Approximately 40 to 50 colonies are tested for the phenotype "growth in the presence of sucrose" and "non-growth in the presence of kanamycin". In 4 colonies exhibiting the phenotype "growth in the presence of sucrose" and "non-growth in the presence of kanamycin", a region of the glk gene, starting from the sequencing primer gl1 (SEQ ID No. 8), spanning the A213V mutation is sequenced by GATC Biotech AG (Constance, Germany) in order to demonstrate that the mutation of the glk_A213V allele is present in the chromosome. The primer gl1 used therefor is synthesized by GATC Biotech AG:

```
                                            (SEQ ID No. 8)
   gl1:
   5' gga aca tga tgc caa ctc ag 3'
```

In that manner a clone is identified that contains the base thymine at position 638 of the coding region of the glk gene and accordingly possesses the glk_A213V allele. That clone is referred to as strain DSM5715glk_A213V.

EXAMPLE 3

Production of Lysine

The *C. glutamicum* strain DSM5715glk_A213V obtained in Example 2 is cultivated in a nutrient medium suitable for the production of lysine, and the lysine content in the culture supernatant is determined.

To that end, the strain is first incubated on agar plate for 24 hours at 33° C. Starting from that agar plate culture, a preliminary culture is inoculated (10 ml of medium in a 100 ml Erlenmeyer flask). MM medium is used as the medium for the preliminary culture. The preliminary culture is incubated for 24 hours at 33° C. at 240 rpm on a shaker. From that preliminary culture, a main culture is inoculated, so that the initial OD (660 nm) of the main culture is 0.1 OD. Mm medium is also used for the main culture.

| MM medium | |
|---|---|
| CSL | 5 g/l |
| MOPS | 20 g/l |
| Glucose (autoclaved separately) | 50 g/l |
| Salts: | |
| $(NH_4)_2SO_4)$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterilized by filtration) | 0.3 mg/l |
| Thiamin * HCl (sterilized by filtration) | 0.2 mg/l |
| L-leucine (sterilized by filtration) | 0.1 g/l |
| $CaCO_3$ | 25 g/l |

CSL (corn steep liquor), MOPS (morpholinopropanesulfonic acid) and the salt solution are adjusted to pH 7 with ammonia water and autoclaved. The sterile substrate and vitamin solutions and the dry autoclaved $CaCO_3$ are then added.

Cultivation takes place in a volume of 10 ml in a 100 ml Erlenmeyer flask with baffles. Cultivation takes place at 33° C. and 80% humidity.

After 72 hours, the OD is determined at a measuring wavelength of 660 nm using a Biomek 1000 (Beckmann Instruments GmbH, Munich). The amount of lysine formed is determined by means of an amino acid analyzer from Eppendorf-BioTronik (Hamburg, Germany) by ion-exchange chromatography and post-column derivation with ninhydrin detection.

The result of the test is shown in Table 1.

TABLE 1

| Strain | OD (660 nm) | Lysine HCl g/l |
|---|---|---|
| DSM5715 | 8.2 | 13.57 |
| DSM5715glk_A213V | 8.8 | 15.22 |

BRIEF DESCRIPTION OF THE FIGURE

FIG. 1: Map of plasmid pK18mobsacB_glk_A213V.

The abbreviations and names used have the following meanings. Where numbers of base pairs are given, they are approximate values which are obtained within the scope of the reproducibility of measurements.

Kan: kanamycin resistance gene

BamHI: cleavage site of the restriction enzyme BamHI

XbaI: cleavage site of the restriction enzyme XbaI glk: glk_A213V allele sacB: sacB gene RP4-mob: mob region having the origin of replication for the transfer (oriT)

oriV: origin of replication V

What is claimed is:

1. An isolated protein comprising the amino acid sequence of SEQ ID NO:2, wherein:
   a) the amino acid at position 213 is an L-amino acid other than L-alanine and
   b) said protein has glucokinase activity.

2. The isolated protein of claim 1, wherein said amino acid at position 213 is L-valine.

3. The isolated protein of claim 1, wherein said amino acid sequence consists of the amino acid sequence of SEQ ID NO:2 but wherein the amino acid at position 213 is an b-amino acid other than L-alanine.

4. The isolated protein of claim 3, wherein said amino acid at position 213 is L-valine.

5. An isolated nucleic acid comprising a nucleotide sequence encoding the protein of any one of claims 1-4.

6. An isolated nucleic acid encoding the protein of claim 4 and having glucokinase activity, said isolated nucleic acid comprising the nucleotide sequence of SEQ ID NO:3.

7. A vector comprising the nucleotide sequence of the nucleic acid of claim 5.

8. A coryneform bacteria transformed with the vector of claim 7.

9. A process for the production of L-lysine or of a feed additive containing L-lysine, comprising:
   a) fermenting the coryneform bacteria of claim 8 under conditions suitable for the production of L-lysine, and
   b) isolating said L-lysine or the fermentation liquor containing said L-lysine.

10. The process of claim 9 wherein said coryneform bacteria are of the species *Coryneform glutamicum*.

11. A process for the production of a composition of L-lysine or of a feed additive containing L-lysine, comprising:
   a) fermenting coryneform bacteria containing a nucleotide sequence encoding the enzyme glucokinase, wherein said glucokinase comprises the amino acid sequence of SEQ ID NO:2 and in the encoded amino acid sequence, L-alanine at position 213 has been replaced by a different proteinogenic amino acid,
   b) concentrating the L-lysine in the fermentation liquor,
   c) isolating said L-lysine or the fermentation liquor containing said L-lysine.

12. The process of claim 11, wherein said amino acid at position 213 is L-valine.

13. The process of either claim 11 or claim 12, wherein said composition of L-lysine or said fermentation liquor comprises >0 to 100% of the constituents of said fermentation liquor and/or of the biomass present during fermentation.

14. An isolated nucleic acid consisting of a nucleotide sequence encoding the protein of any one of claims 1-4.

15. An isolated nucleic acid, encoding the protein of claim 4, wherein said nucleic acid consists of the nucleotide sequence of SEQ ID NO:3.

* * * * *